United States Patent
Reinschke et al.

(10) Patent No.: US 7,663,458 B2
(45) Date of Patent: Feb. 16, 2010

(54) COIL SYSTEM FOR CONTACT-FREE MAGNETIC NAVIGATION OF A MAGNETIC BODY IN A WORKING CHAMBER

(75) Inventors: Johannes Reinschke, Nürnberg (DE); Günter Ries, Erlangen (DE); Rudolf Röckelein, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/884,724

(22) PCT Filed: Mar. 1, 2006

(86) PCT No.: PCT/EP2006/060375

§ 371 (c)(1),
(2), (4) Date: May 14, 2008

(87) PCT Pub. No.: WO2006/092421

PCT Pub. Date: Sep. 8, 2006

(65) Prior Publication Data

US 2008/0272873 A1    Nov. 6, 2008

(30) Foreign Application Priority Data

Mar. 4, 2005   (DE) ............... 10 2005 010 489

(51) Int. Cl.
*H01F 5/00*   (2006.01)

(52) U.S. Cl. ............................................. 335/299

(58) Field of Classification Search ............ 335/299
See application file for complete search history.

(56) References Cited

U.S. PATENT DOCUMENTS

| | | |
|---|---|---|
| 5,125,888 A | 6/1992 | Howard et al. |
| 5,349,294 A | 9/1994 | Kasuboski |
| 5,406,205 A | 4/1995 | Müller |
| 5,707,335 A | 1/1998 | Howard et al. |
| 6,241,671 B1 | 6/2001 | Ritter et al. |
| 6,529,761 B2 | 3/2003 | Creighton, IV et al. |
| 6,707,302 B2 | 3/2004 | Ries |
| 6,717,409 B2 | 4/2004 | Kimmlingen et al. |
| 7,173,507 B2 | 2/2007 | Ries |
| 2003/0060702 A1 | 3/2003 | Kuth et al. |
| 2003/0125752 A1 | 7/2003 | Werp et al. |

FOREIGN PATENT DOCUMENTS

| | | |
|---|---|---|
| WO | WO 96/03795 | 2/1996 |
| WO | WO 00/13586 | 3/2000 |

OTHER PUBLICATIONS

"Electrical Stimulation for Propelling Endoscopes," Mosse et al., Gastrointestinal Endoscopy, vol. 54, No. 1 (2001) pp. 79-83.
"Optimal Realization of Arbitrary Forces in a Magnetic Stereotaxis System," Meeker et al., IEEE Trans. on Magnetics, vol. 32, No. 2 (1996) pp. 320-328.

*Primary Examiner*—Ramon M Barrera
(74) *Attorney, Agent, or Firm*—Schiff Hardin LLP

(57) ABSTRACT

A magnetic body is displaceable in a contact-free manner in a working chamber by the use of a magnetic coil system composed of fourteen individually controllable coils. Three magnetic field components and five magnetic field gradients are produced. Apart from two individual coils in the coil system, the other coils, which may be saddle-shaped coils, are arranged on lateral tubular surfaces surrounding the working chamber.

17 Claims, 2 Drawing Sheets

COIL SYSTEM FOR CONTACT-FREE MAGNETIC NAVIGATION OF A MAGNETIC BODY IN A WORKING CHAMBER

BACKGROUND OF THE INVENTION

1. Field of the Invention

The invention concerns a coil system of the type having multiple of individual coils that can be activated individually for contact-free magnetic navigation of a magnetic body in a three-dimensional working space accessible in the z-direction of an orthogonal x, y, z coordinate system.

2. Description of the Prior Art

A coil system of the above type is known from "IEEE Transactions on Magnetics", Vol. 32, No. 2, Mar. 1996, pages 320 through 328.

In medicine, endoscopes and catheters are used that are inserted via incisions or body openings and can be displaced from the outside of the body in their longitudinal direction, and thus are navigable only in one dimension. An optical examination is possible with light guides, whereby an endoscope tip (and therewith the viewing direction) can be panned via control wires. Additional devices, in particular for biopsy, can be placed in a working channel in the catheter. These types of probes, however, are navigable only in a limited manner, particularly when encountering branches that are located at points further removed from a body opening. The ability to apply a contact-free force to assist navigation in such situations would expand the applications in which such devices could be used.

A magnetic coil system for a contact-free magnetic probe control is known from the aforementioned publication as well as U.S. Pat. No. 5,125,880. Such a magnetic coil system has six (advantageously superconducting) individual coils that are arranged on the faces of a cube whose position can be mathematically described in an orthogonal x, y, z coordinate system. Variable field directions and field gradients are generated with these coils in order to direct or to move a catheter with magnetic material or magnetic implants into a (for example human) body to be examined for therapy purposes. Unlimited navigation freedom of the magnetic body, however, cannot be achieved with a magnetic coil system composed of six individual coils.

The generation of magnetic field gradients is known from MRI (magnetic resonance imaging) systems for medical diagnostics. A coil system for this purpose is known, for example, from DE 39 37 148 C2.

It is also known to utilize such field gradients for determination of the momentary position and alignment of an object (such as, for example, a catheter) in a three-dimensional working space (such as, for example, a human body). A corresponding apparatus is known from WO 00/13586 A. For this purpose, the apparatus has a field generator for generation of MRI gradient fields with which electrical voltages are induced in sensor coils of the object. These electrical voltages are then relayed to signal processing electronics via a conductor system connected with the object. Contact-free, magnetically controllable movement of the object, however, is not possible.

A magnetic coil system with three coils is described in U.S. Pat. No. 6,241,671, and U.S. Pat. No. 6,529,761 discloses an arrangement of a few permanent magnets arranged such that they can rotate around a patient, the field of these permanent magnets being influenced by magnetic screens and that can generate a magnetic wave for movement of a magnetic probe.

Magnetic coil systems with rotatable permanent magnets for controlling magnetic catheters, in particular under x-ray monitoring, are also known. Nothing is said in this prior art about methods for a position stabilization of magnetic probe bodies via feedback; it is assumed that a magnetic probe body, specified by field direction and gradient, always rests on an inner surface within a body to be examined.

A method with additional pulse coils with which a magnetic probe is moved in steps via precisely defined current pulses under computer monitoring is described in WO 96/03795 A1.

Devices known as video capsules are also known (for example from the periodical "Gastrointestinal Endoscopy", Vol. 54, No. 1, pages 79 through 83) that serve for examination of the alimentary canal. The movement of the video capsule occurs via the natural intestinal movement, meaning that the locomotion and viewing direction are random.

A corresponding video capsule that is equipped with a rod magnet as well as with video and other intervention devices is described in DE 101 42 253 C1. An external magnetic coil system exerts forces on the rod magnet for navigation. A free-floating mode (known as a helicopter mode) with external control via a 6D mouse, feedback of force via the mouse, and position feedback via a transponder are mentioned. Details for realization of the magnetic coil system and for operation of its individual coils are not provided.

A magnetic coil system for contact-free navigation or movement of a (ferro)magnetic body (such as, for example, a rod magnet) in a working space is proposed in unpublished DE patent application 103 40 925.4 from 5 Sep. 2003. The body is aligned in the working space and/or a force is to be exerted on the body with this magnetic system. The alignment as well as the magnitude and direction of the force on the body are magnetic and can be predetermined from the outside without a mechanical connection. For this purpose, a three-dimensional working space is assumed that is surrounded by surfaces stretching in a right-angled x, y, z coordinate system. The coil system has fourteen individually controllable individual coils that are fashioned for generation of the three magnetic field components $B_x$, $B_y$, $B_z$ as well as the generation of five magnetic field gradients from the symmetrical (with regard to its diagonal D) gradient matrix $$D \searrow \begin{pmatrix} \dfrac{dB_x}{dx} & \dfrac{dB_y}{dx} & \dfrac{dB_z}{dx} \\ \dfrac{dB_x}{dy} & \dfrac{dB_y}{dy} & \dfrac{dB_z}{dy} \\ \dfrac{dB_x}{dz} & \dfrac{dB_y}{dz} & \dfrac{dB_z}{dz} \end{pmatrix}_{\searrow},$$

whereby two of the diagonal elements of the gradient matrix and one of the outer diagonal elements from the three symmetrical (relative to the diagonal) gradient element pairs of the gradient matrix are to be generated with the individual coils.

In the proposed magnetic coil system surrounding the working space like a cage, it is assumed that, due to the conditions rotH=0 and divB=0 imposed by the Maxwell equations—whereby the quantities indicated in bold print symbolize vectors, only three independent gradients of the possible six field gradients $dB_x/dy$, $dB_x/dy$, $dB_y/dx$, $dB_y/dz$, $dB_z/dx$ and $dB_z/dz$ must be generated and only two of the three field gradients $dB_x/dx$, $dB_y/dy$ and $dB_z/dz$. Eight different current patterns (corresponding to the eight magnetic degrees of freedom) must be able to be impressed on the fourteen individual coils with currents of equal magnitude. These current patterns each predominantly generate a field component or a field gradient. Every combination of magnetic field components and field gradients allowable according to the Maxwell equations can then be generated by superimposition.

A contact-free control/movement (=navigation) of a magnetic body in the sense of a (mechanical) contact-free alignment of this body and/or of a force exertion on this (for example a probe connected with a magnetic element such as, for example, a catheter, endoscope or a video capsule according to DE 101 42 253 C1) by means of magnetic fields in a working space is enabled in this manner.

The following design features can additionally be provided individually or in combination with one another for the proposed magnetic system.

The fourteen individually controllable individual coils can thus be arranged on paired surfaces situated opposite one another and at least one tube-shaped generated surface extending in the z-direction. The faces of a cuboid or cube can thereby be spanned up to the generated surface. They do not necessarily need to be fashioned flat.

At least six of the individual coils can thereby lie on the paired, opposite frontal surfaces or lateral surfaces of the working space and serve for generation of the three magnetic field components $B_x$, $B_y$, $B_z$ as well as the two diagonal elements of the gradient matrix. At the same time at least four of the individual coils can be arranged distributed on the at least one tube shaped generated surface surrounding the working space (as viewed in the circumferential direction) and serve for generation of at least one extra-diagonal element of the gradient matrix. The required three extra-diagonal elements can thus be formed together with the remaining individual coils.

For this purpose, six of the individual coils can be situated as three coil pairs on the paired, opposite frontal or, respectively, lateral surfaces of the working space and eight of the individual coils form two coil arrangements that are situated one after another (viewed in the z-direction) on the at least one tube-shaped generated surface, and whose respective four individual coils are arranged distributed on the generated surface (viewed in the circumferential direction) and serve for generation of the three extra-diagonal elements of the gradient matrix.

Instead of this, in the proposed coil system a coil pair of individual coils can lie on the frontal surfaces of the working space and serves for generation of the magnetic field component $B_z$ as well as the diagonal element $dB_z/dz$ of the gradient matrix, a respective coil arrangement can be composed of respectively two individual coils arranged one after another (viewed in the z-direction) lies on the paired, opposite lateral surfaces and serves for generation of the magnetic field component $B_x$ or, respectively, $B_y$, a coil arrangement made in particular of four individual coils can be distributed (as viewed in the circumferential direction) on the at least one tube-shaped generated surface and the coil arrangement on the lateral surfaces and the generated surface can serve for generation of a further diagonal element and the three extra-diagonal elements of the gradient matrix.

The at least one generated surface can be located within the inner space spanned by the six paired, opposite surfaces.

Given the embodiments rendered in the preceding the field gradient coils situated on the (imaginary) generated surface are designed saddle-shaped. It is thereby possible that their frontal arc segments running in the circumferential direction on the generated surface lie next to one another (as viewed in the circumferential direction), i.e. respectively occupy an arc angle of >90° or overlap.

Moreover, at least some of the field component coils can be designed as planar rectangular coils or circular coils.

Coil pairs and/or coil arrangements can respectively be formed from individual coils with identical shape.

The coil pairs composed of individual coils can be arranged orthogonal to one another for generation of the magnetic field components.

Parts made from magnetically soft material can also be associated with the outside of the coil system for field amplification and/or field shielding.

Means for detection of the position of the magnetic body within the working space can also be provided.

In general a computer is used to control the fourteen individual coils of the magnetic coil system in that it controls their respectively associated current feed dependent on the respective position of the magnetic body to be moved.

In the proposed magnetic coil system a circular cylinder formed by one of eight saddle coils is thus enclosed by a cuboid comprising six Helmholtz coils.

SUMMARY OF THE INVENTION

An object of the present invention to improve the magnetic coil system described immediately above so that the power requirement for operation of the system is reduced.

This object is achieved in accordance with the invention by a magnetic coil system having fourteen individually controllable individual coils for contact-free magnetic navigation of a magnetic body in a three-dimensional working space accessible in the z-direction of an orthogonal x, y, z coordinate system, wherein the individual coils are fashioned for generation of the three magnetic field components $B_x$, $B_y$ and $B_z$ as well as of five magnetic field gradients from the (with regard to its diagonal D) symmetrical and spur-free gradient matrix GM $$GM = \begin{pmatrix} \dfrac{dB_x}{dx} & \dfrac{dB_y}{dx} & \dfrac{dB_z}{dx} \\ \dfrac{dB_x}{dy} & \dfrac{dB_y}{dy} & \dfrac{dB_z}{dy} \\ \dfrac{dB_x}{dz} & \dfrac{dB_y}{dz} & \dfrac{dB_z}{dz} \end{pmatrix}^{D_\searrow}.$$

Two of the three diagonal elements of the gradient matrix GM and one of the extra-diagonal elements can be generated with the individual coils from the three gradient element pairs of the gradient matrix GM that are symmetrical to the diagonal. At least six of the individual coils should be provided for generation of the three magnetic field components $B_x$, $B_y$, $B_z$ as well as the two diagonal elements of the gradient matrix GM, of which at least six individual coils at least two are situated on frontal surfaces of the coil system and the remaining individual coils of the coil system lie on at least one first, tube-shaped generated surface extending in the z-direction and enclosing the working space.

The invention is based on the insight that a comparably lower power requirement can be achieved with a modified geometry of the Helmholtz coils of the proposed magnetic coil system. This saves operating costs and production costs of the overall system because the required power amplifiers with which the coil currents of the individual coils are controlled as well as the cooling system can be designed for a lower maximum power.

The magnetic coil system according to the invention can exhibit the following features or be designed according to the following:

In the coil system at least four of the individual coils can thus be situated distributed (as viewed in the circumferential direction) on at least one further, tube-shaped generated surface surrounding the working space.

Preferably six of the individual coils can thereby be situated in pairs on the opposite frontal surfaces or, respectively, the at least one first generated surface and eight of the individual coils can form two coil arrangements that are situated one after another (as viewed in the z-direction) on the at least one further generated surface, and whose four respective individual coils are arranged distributed (as viewed in the circumferential direction) on the further generated surface.

In principle, in the coil system the at least one further generated surface can be located within the at least one first generated surface. It is also possible that the individual generated surfaces are respectively formed from a concentric arrangement of a number of generated surfaces. Moreover, a radial separation can be maintained between the individual coils situated on the first generated surface and the individual coils situated on the further generated surface. It is also possible for the enveloping outer surface of the inner individual coils to directly form the first generated surface for the outer individual coils as no radial separation is present.

The field component coils situated on the at least one first generated surface and/or the field gradient coils situated on the at least one further generated surface are designed saddle-shaped. The saddle-shaped field component coils can thereby in particular be arranged rotated by at least approximately 45° (as viewed in the circumferential direction) relative to the saddle-shaped field gradient coils.

Moreover, the frontal arc sections of adjacent saddle-shaped coils can advantageously be situated next to one another or overlap (as viewed in the circumferential direction).

The frontal field component coils can be designed as flat toroids that can preferably lie on the further generated surface of the field gradient coils.

With regard to a limitation of the power requirement of the coil system, it is thereby particularly advantageous when the length of the coil arrangement made from the saddle-shaped field component coils is smaller in the z-direction (advantageously smaller by 10 to 25%) than the corresponding length of the coil arrangement made from the toroids and the field gradient coils.

Coil pairs and/or coil arrangements can be formed from individual coils with identical shape.

Instead of this, in principle it is also possible that coil pairs and/or coil arrangements are respectively formed from individual coils with different coil cross-section. This means that the individual coils within a coil pair do not necessarily need to exhibit identical diameter.

For generation of the magnetic field components, coil pairs arranged orthogonal to one another, which coil pairs are made from individual coils, are generally provided.

With regard to an optimization of the power requirement it is particularly advantageous when individual coils with different winding cross-section and/or cross-section of their conductors are used. In particular the individual coils can possess varying winding cross-sections on various generated surfaces. A winding cross-section is thereby the winding strand generally formed from a plurality of conductors. Conductors with different aspect ratios (ratio of wide side to narrow side) can also advantageously be used.

Arbitrary electrical conductors can be used for the inventive coil system. Naturally, a use of conductors to be cooled (such as, for example, of metallic low-$T_c$ or oxidic high-$T_c$ superconductors) is also possible. A cooling of at least individuals of the individual coils [sic] can therefore be required.

Additional parts made from magnetically soft material can be provided on the outside of the coil system for a field amplification and/or field shielding.

The coil system is preferably further equipped with means for a detection of the position of the magnetic body within the working space.

In general the individual coils of the coil system are controlled in a known manner with the aid of a computer.

DESCRIPTION OF THE PREFERRED EMBODIMENTS

Figure 1:
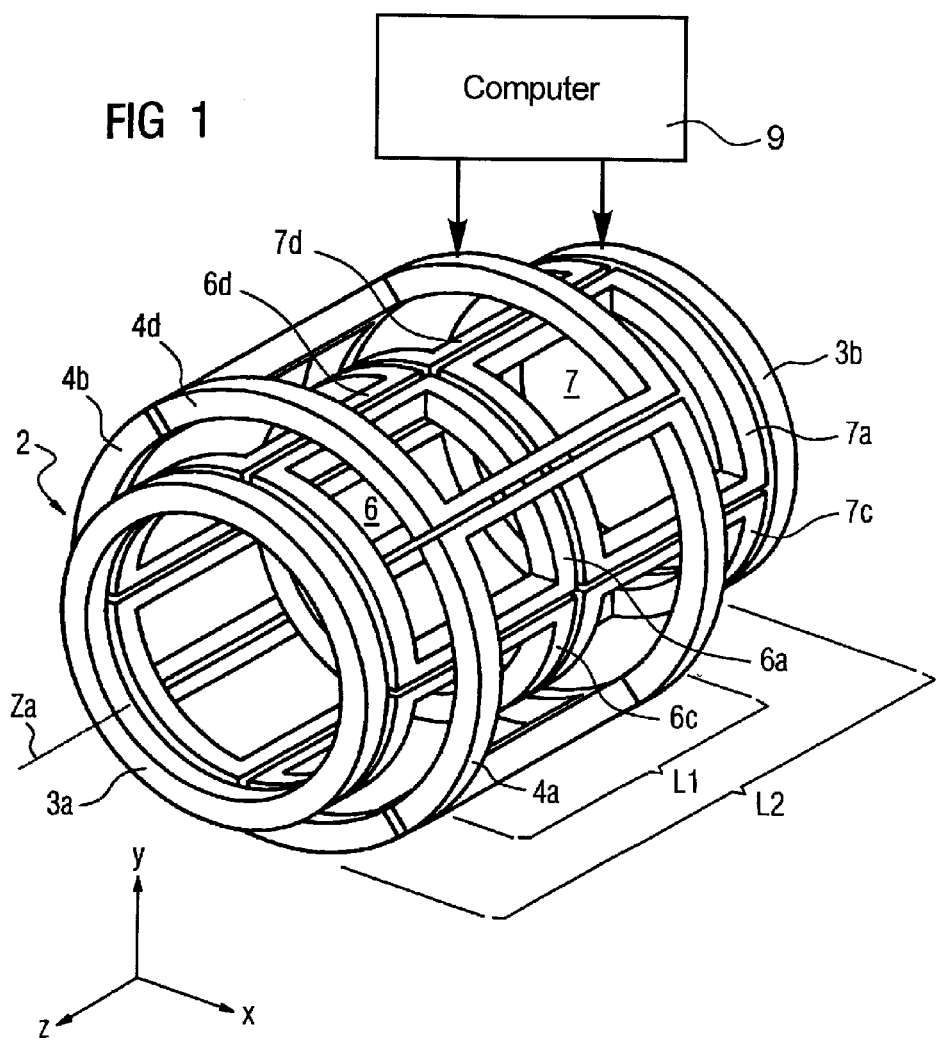
FIG. 1 illustrates a coil system constructed and operating in accordance with the present invention in a perspective view.

A magnetic sample body can move without contact in a working volume with a magnetic coil system according to the invention. The size and the direction of the force and the torque on this sample body can be predetermined magnetically and without mechanical connection from the outside. In particular in applications in medicine a probe equipped with such magnetic sample body can be a catheter or an endoscope with magnetic element or a small television camera with illumination and transmitter that sends video images from the inside of the body (such as, for example, the alimentary canal). Moreover, ferromagnetic foreign bodies such as, for example, a needle or function modules in objects or spaces inaccessible from the outside can be moved or removed via magnetic forces. In addition to the application in medicine, a usage of an inventive magnetic coil system is also just as well possible in other fields such as, for example, in contaminated spaces (such as, for example, of containers). Other (in particular inaccessible) objects can also be inspected (for example internally) with associated magnet probes, whereby the probes can naturally also be equipped with other or additional functionality.

As an exemplary embodiment of such a ferromagnetic body, a probe is subsequently described with which the ferromagnetic material is associated or that embodies parts made from such a material. The ferromagnetic body or probe can therefore also be designated as a "magnetic body" or "magnetic probe".

With the aid of the magnetic coil system the magnetic body (and therewith the probe) can be externally controlled via magnetic forces in all three lateral degrees of freedom and in two rotational degrees of freedom in the viewing direction. Moreover, the magnetic coil system advantageously allows access in the z-direction from the outside, for example in order to be positioned in the working space inside persons to be treated.

The Figures show a typical exemplary embodiment of an inventive magnetic coil system with which navigation or spatial control and/or movement of a magnetic body are enabled by forces acting on the body that are produced of magnetic fields. The mode of action of the coil system is analogous to that of the magnetic coil system as described in the unpublished patent application cited earlier. In the coil system, a circular cylinder (preferably formed from one of eight saddle coils) is surrounded by a cuboid formed from six Helmholtz coils. In the inventive magnetic coil system eight saddle coils are in fact likewise correspondingly provided; however, these are surrounded by four further saddle coils that replace the four lateral Helmholtz coils of the cuboid arrangement of the earlier system. Instead of the two remaining frontal Helmholtz coils with cuboid design, circular individual coils are henceforth provided on the face sides. A correspondingly executed magnetic coil system is generally designated with 2 in the Figures. In the Figures parts (not shown in detail) correspond to those of the magnetic coil system from the unpublished patent application.

Based on a concrete exemplary embodiment of an inventive magnetic coil system 2 with design shown in the Figures, it can be achieved that, relative to the embodiment of a magnetic system according to the unpublished patent application with cuboid arrangement of its rectangular field component coils, an approximate 20% reduction of the electrical power requirement is provided with the inventive design of the field component coils given identical copper proportion of the conductors.

The inventively executed magnetic coil system 2 in particular has an at least approximately hollow cylinder-shaped design. Its individual coils thereby lie at least in large part on at least two concentrically enclosing generated cylinder surfaces, of which a first is designated with MF1 and surrounds a second surface MF2 (see in particular FIG. 2). An orthogonal x, y, z coordinate system whose z-direction is established by the cylinder axis designated with Za is associated with the hollow cylinder design. Surfaces situated orthogonal to the z-direction and demarcating a coil arrangement in the z-direction are thereby designated as frontal surfaces. The inner second generated surface MF2 encloses a three-dimensionally shaped inner or working space (designated with A) that is accessible from at least one of the facing sides in the direction of the cylinder axis Za. The aforementioned generated surfaces are generally imaginary surfaces. However, the individual coils of the magnetic coil system 2 extending on said generated surfaces are naturally held by concrete fixing means (not shown in the Figures).

The magnetic coil system 2 according to the invention has fourteen normally conducting or superconducting individual coils that are advantageously fashioned as toroids or, respectively, saddle coils. In the figures the winding shapes are thereby only schematically represented; individual coils with coil shapes slightly deviating therefrom can also be selected. The coil system of the selected exemplary embodiment thereby comprises six field component coils 3a, 3b, 4a, 4b and 4c, 4d as well as eight field gradient coils 6a through 6d and 7a through 7d. The field components $B_x$, $B_y$, $B_z$ as well as at least two of the three diagonal magnetic field gradients $dB_x/dx$, $dB_y/dy$ and $dB_z/dz$ from the gradient matrix reproduced in the following are to be generated with the field component coils 3a, 3b or, respectively, 4a, 4b or, respectively, 4c, 4d situated oppositely in pairs. This gradient matrix has the following configuration:

$$GM = \begin{pmatrix} \dfrac{dB_x}{dx} & \dfrac{dB_y}{dx} & \dfrac{dB_z}{dx} \\ \dfrac{dB_x}{dy} & \dfrac{dB_y}{dy} & \dfrac{dB_z}{dy} \\ \dfrac{dB_x}{dz} & \dfrac{dB_y}{dz} & \dfrac{dB_z}{dz} \end{pmatrix}$$

A line connecting the elements $dB_x/dx$, $dB_y/dy$ and $dB_z/dz$ is defined as a diagonal D of the gradient matrix GM. The gradient matrix GM is established symmetrically relative to this diagonal D or the aforementioned magnetic field gradients situated on it. The sum of the diagonal elements is equal to zero, meaning that the gradient matrix GM is spur-free. The coil pairs (with current carrying directions to be selected in them) generating the individual field components are specified in the cited DE patent application. Pairs of the field component coils are advantageously arranged orthogonally among one another. In general they have identical shape at least per pair.

Two coil arrangements 6 and 7 that are arranged in succession (as viewed in the z-direction) are respectively fashioned with the eight field gradient coils (which are saddle-shaped in design) 6a through 6d and 7a through 7d. The saddle-shaped field gradient coils surround the working space A in terms of field, whereby they are mutually arranged on the at least one imaginary second generated surface MF2. The gradient coils belonging to a coil arrangement are mutually spaced or lie on one another (as viewed in the circumferential direction); this means that an interstice (even if only slight) can respectively be present between their frontal arc sections and thus between their longitudinal sides running in the z-direction. An overlapping of adjacent gradient coils on their longitudinal sides is also possible. The imaginary second generated surface MF2 advantageously has a circular cross-section. However, if applicable it can also have a different (for example quadratic) cross-sectional shape. Instead of a single generated surface MF2, concentric generated surfaces care also possible on which the individual coils from one or from both coil arrangements are located. The at least one generated surface MF2 also does not necessarily need to be situated within the space enclosed by the field component coils 3a, 3b, 4a, 4b, 4c, 4d, but rather can possibly also enclose the structure made from these coils. In general at least the field gradient coils belonging to a coil arrangement 6 and/or 7 have the same shape.

Figure 2:
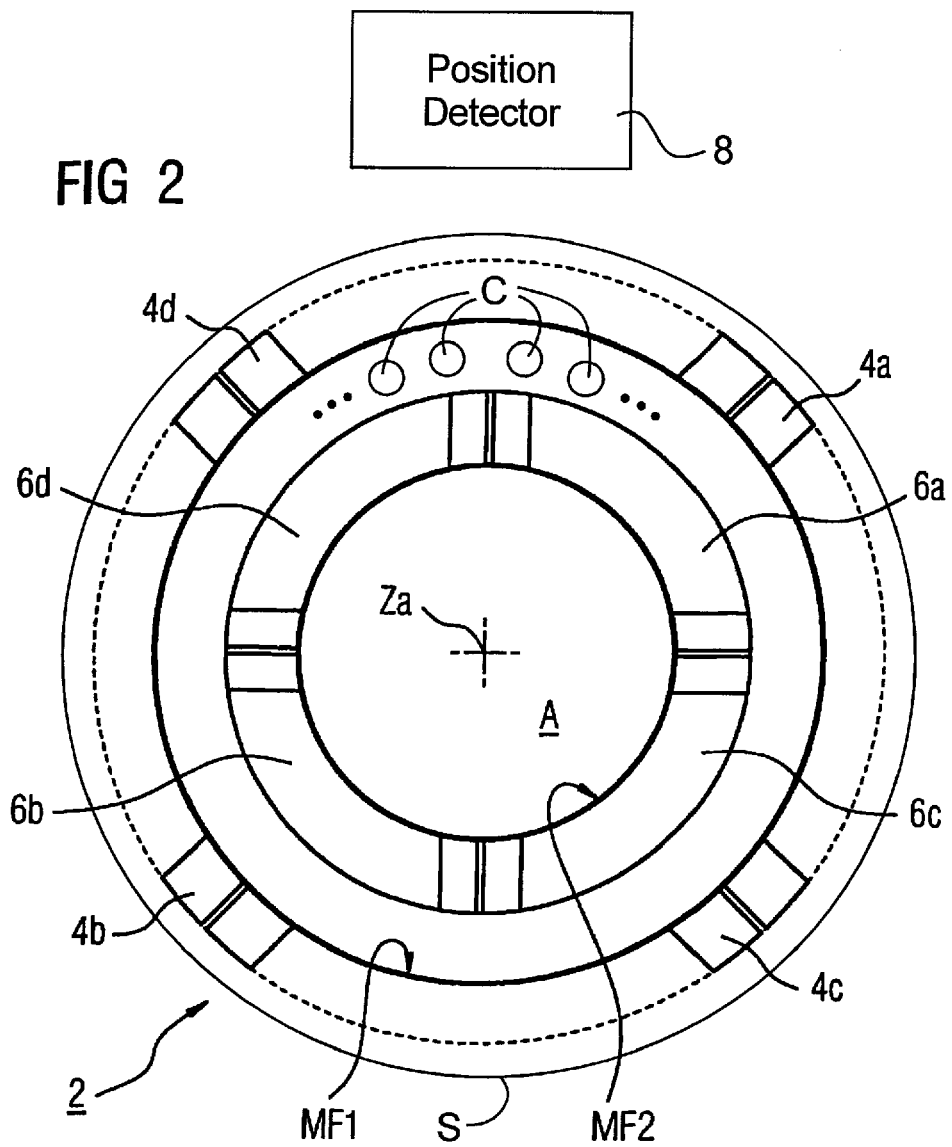
FIG. 2 is a cross-section through the coil system of FIG. 1.

In particular from FIG. 2 can be seen that the two generated surfaces MF1 and MF2 are radially separated so far that a certain radial distance is present between the enveloping hollow cylindrical outer surface around the inner individual coils 6a through 6d and the outer generated surface for the individual coils 4a through 4d. Such a distance is not absolutely necessary. Rather, the outer generated surface MF1 can also form the enveloping outer surface of the inner individual coils.

As can be seen from FIG. 1, with regard to a reduction of the power requirement of the magnetic coil system 2 or its fourteen individual coils an embodiment is advantageously selected in which the outer four saddle coils 4a through 4d have a distinctly shorter (advantageously by at least 10%, in particular by 25%) axial extent or, respectively, length L1 than the circular cylinder with an axial length L2 that is formed by the toroids 3a, 3b as well as the eight inner saddle coils 6a through 6d and 7a through 7d. For the front toroids 3a and 3b such a radius is thereby advantageously selected that is situated on the generated surface together with the field gradient coils 6a through 6d and 7a through 7d. Moreover, it is advantageous when the arrangement of the outer saddle-shaped field component coils 4a through 4d is selected with regard to the field gradient coils 6a through 6d and 7a through 7d surrounded by it so that it is offset/rotated by at least approximately 45° (as viewed in the circumferential direction), meaning that their respective longitudinal sides do not come to lie atop one another. This arrangement is in particular apparent from the cross-section of FIG. 2. The section of the Figure is thereby placed in the region of the facing sides of the field gradient coils 6a through 6d.

For example, magnetic field gradients $dB_x/dy$, $dB_z/dx$ and $dB_z/dy$ are to be formed with the field gradient coils 6a through 6d and 7a through 7d given selection of suitable current conduction directions. These three field gradients respectively represent an extra-diagonal element of the preceding gradient matrix GM. These elements thereby respectively originate from a different element pair that is symmetrical relative to the diagonal D. Namely, given the formation of corresponding field gradients, the field gradients that are symmetrical relative to the diagonal D are inevitably generated in pairs. In this case these would be the gradients $dB_y/dx$ or $dB_x/dz$ or $dB_y/dz$. Moreover, since only five gradient degrees of freedom are to be taken into account no particular current pattern is needed for the $dB_z/dz$ field gradient. Alternatively, however, the $dB_z/dz$ field gradient can be generated and one of the gradients $dB_x/dx$, or $dB_y/dy$, can therefore be omitted. This means that only two of the three gradients lying on diagonal D of the gradient matrix must be generated.

Depending on the current flow direction, the magnetic field component $B_z$ or, respectively, the field gradient $dB_z/dz$ is thereby to be generated with the pair made up of the individual coils 3a, 3b. The field component $B_y$ or the field gradient $dB_y/dy$ is to be formed in a corresponding manner with the pair composed of the individual coils 4c, 4d. The coil pair made up of the individual coils 4a and 4b generates the field component $B_x$. Depending on the current conduction direction in the individual coils, the field gradients $dB_z/dx$ or, respectively, $dB_z/dy$ or, respectively, $dB_x/dy$ are to be generated with the two coil arrangements 6 and 7 made up of the respective four gradient coils 6a through 6d or, respectively, 7a through 7d.

If an elongated magnetic body (for example a ferromagnet or permanent magnet) that is, for example, connected with a probe is now introduced into the working space A of the magnetic coil system 2, it attempts to align parallel to the field direction, whereby it thus also predetermines the alignment of the probe. The field gradients thereby exert a force F=degree(m·B) on the magnetic body, whereby m is the vector of the magnetic moment of the magnetic body. By a targeted activation of each of the fourteen individual coils it is then possible that the magnetic body can be arbitrarily aligned in the working space A and that a predetermined force F is also to be exerted on it in all directions, thus that it can not only be rotated but rather can also be moved or, respectively, displaced linearly.

In addition to the respective desired field components, each current pattern generates other field components in the inventive magnetic coil system. These depend on the respective coil dimensions and the location of the magnetic body; their amplitude increases from the center in the direction towards the windings of the coils. This means that a simpler correlation between the current strength of the current pattern with the field direction and force direction F=degree(m·B) is not provided at a location of the magnetic body.

However, precisely those fields and field gradients which generate the desired alignment and force effect on the magnetic body are to be adjusted at a magnetic body location via a suitable superimposition of the eight current patterns in the fourteen individual coils. For example, a free flotation of the magnetic body in space can be realized particularly advantageously when precisely the weight F=m·g=degree(m·B) is generated (m=mass, g=acceleration due to gravity). The calculation in this regard advantageously ensues with a computer that in particular implements the following calculation steps and possibly runs repeatedly during a movement of the magnetic body:

calculation of the desired values of the three field components $B_x$, $B_y$, $B_z$ at the magnetic body location from a predetermined magnetic body direction in polar coordinates $\theta$ and $\phi$ in the working space and the magnitude $|B|$;

calculation of the desired values of the five independent field gradients $dB_x/dx$, $dB_y/dy$, $dB_x/dy$, $dB_z/dx$ and $dB_z/dy$ from a predetermined magnetic force on the magnetic body; the gradient $dB_z/dz$ can also be provided and one of the other gradients $dB_x/dx$ or $dB_y/dy$ lying on the diagonal of the gradient matrix can therefore be made zero. Superimpositions of the gradient $dB_z/dz$ with one of the other diagonal gradients $dB_x/dx$ or $dB_y/dy$ are also conceivable;

calculation of field components and field gradients at the magnetic body location for each of the eight current patterns from the coil geometry, for example for 1 A coil current, and representation in the form of an 8×8 matrix;

calculation of an inverse matrix. This inverse matrix depends only on the coil geometry and can be generated in advance for every point on a grid in the provided working space. During the operation of the device interpolation occurs between the values in this grid for faster calculation;

multiplication of the inverse matrix for the magnetic body location with the field vector ($B_x$, $B_y$, $B_z$, $dB_x/dx$, $dB_y/dy$, $dB_x/dy$, $dB_z/dx$, $dB_z/dy$) yields the current values for the eight current patterns;

division of the current patterns to the fourteen individual coils according to respective positive or negative current direction from stored table and linear superimposition of the currents in the individual coils;

activation of the fourteen power supplies for the individual coils;

monitoring of the loss power limits in the individual coils.

A corresponding device for activation of the fourteen individual coils advantageously interacts with an imaging device serving as a position detector 8 for monitoring the magnetic body or, respectively, probe position. A computer 9 with which the required fourteen power supplies are to energize the magnetic coil system 2 is used for this. In addition to freely predetermined field direction, unlimited magnetic forces are thus to be exerted on a magnetic body or, respectively, a corresponding probe in all three spatial directions with the aid of the fourteen individual coils. Further equipment can naturally be associated. For example, an x-ray apparatus with an x-ray tube can be provided whose radiation permeates the free space between the windings of the individual coils. The position or movement of the magnetic body can then be monitored on a screen outside of the magnetic coil system.

The following measures are provided for a practical embodiment of the magnetic coil system according to the representations of the Figures:

the individual coils can be wound from aluminum or copper strips and are possibly liquid-cooled via conduits C. Copper conductors with rectangular cross-section are particularly advantageous with regard to a high electrical conductivity and a high conductor filling degree.

The individual coils can also be produced from hollow metal sections through whose inner space a coolant medium is possibly conducted.

The individual coils can in particular be generated from superconducting conductors, advantageously with high-$T_c$ superconducting material, and be correspondingly cooled.

Naturally further individual coils can also be used, for example for homogenization of the magnetic field.

Moreover, magnetic material can be associated with the magnetic coil system. For example, it can be at least partially enclosed by parts made from such material. Magnetic return bodies made from magnetically soft material (such as iron) can thus be provided that enclose the gradient coils of the system 2 from the outside. In particular a field amplification in the working space A and/or a scatter field shielding S from the outside is achieved with such magnetically soft parts.

Different conductor cross-sections can possibly be selected for the individual coils of a coil pair for generation of the magnetic field components or a coil arrangement for generation of the field gradients. The conductor cross-sections of the inner eight saddle coils 6a through 6d and 7a through 7d on the generated surface MF2, the outer saddle coils 4a through 4d and both frontal toroids 3a and 3b can correspondingly be different in size and aspect ratio (ratio of width (in the circumferential direction) to height (in the radial direction)). It is particularly advantageous to make the eight inner saddle coils 6a through 6d and 7a through 7d and the two toroids 3a and 3b higher than they are wide in the cross-section of their winding, whereas a cross-section with greater width than height is provided for the four outer saddle coils 4a through 4d. The winding cross-section is formed by the sum of the cross-sections of the conductors (conductor windings) forming them or, respectively, of a winding strand of a coil. Corresponding cross-section ratios are indicated in FIG. 2. For example, the aspect ratio in an outer saddle coil (for example 4d) is ≈1.4 and that of an inner saddle coil (for example 6d) is ≈0.8.

In the exemplary embodiments of the inventive magnetic coil system 2 shown using the preceding Figures it was assumed that, in addition to the field components $B_x$, $B_y$ and $B_z$, two of the three diagonal field gradients according to the preceding gradient matrix GM are to be generated with the paired, opposite field component coils. However, it is also possible to generate extra-diagonal field gradients with field component coils. For this it is necessary that at least one (in particular two) of the three field component coils be formed by coil pairs made up of individual coils.

In the inventive magnetic coil system 2 not all three diagonal gradient elements are to be generated. Namely, since only two of these elements are required, one of the corresponding current patterns of the third element can be foregone. It is thereby insignificant which current pattern for which element is omitted. In addition to this it is also possible to generate only one gradient. The second gradient can then be formed via a linear combination of the two other gradients, whereby the ratio of the coil currents is fixed and independent of the current value. This means that gradients can also always be generated via corresponding linear combinations of the coil currents from various individual coils. This naturally applies for the embodiment of the magnetic coil system 2 according to the figures.

Although modifications and changes may be suggested by those skilled in the art, it is the invention of the inventors to embody within the patent warranted hereon all changes and modifications as reasonably and properly come within the scope of their contribution to the art.

The invention claimed is:

1. A coil system for contact-free magnetic navigation of a magnetic body in a three-dimensional working space accessible in the z-direction of an orthogonal x, y, z coordinate system, said coil system comprising fourteen individually controllable individual coils that generate three magnetic field components $B_x$, $B_y$ and $B_z$ and five magnetic field gradients from a diagonally symmetrical and spur-free gradient matrix GM $$GM = \begin{pmatrix} \frac{dB_x}{dx} & \frac{dB_y}{dx} & \frac{dB_z}{dx} \\ \frac{dB_x}{dy} & \frac{dB_y}{dy} & \frac{dB_z}{dy} \\ \frac{dB_x}{dz} & \frac{dB_y}{dz} & \frac{dB_z}{dz} \end{pmatrix},$$

wherein two of the three diagonal elements of the gradient matrix GM and one of the extra-diagonal elements are to be generated with the individual coils from the three gradient element pairs of the gradient matrix GM that are symmetrical to the diagonal;

wherein at least six of the individual coils are provided, of which at least two are situated on frontal surfaces of the coil system and remaining individual coils of the coil system lie on at least one non-quadric, tube-shaped generated surface extending in the z-direction and enclosing the working space; and wherein at least four of the individual coils are distributed in a circumferential direction of the coil system on at least one further, non-quadratic tube-shaped generated surface surrounding the working space, said at least one further generated surface being located within the at least one first generated surface.

2. A coil system according to claim 1, wherein six of the individual coils are situated in pairs on opposite frontal surfaces of the at least one first generated surface; and eight of the individual coils form two coil arrangements that are situated one after another in the z-direction on the at least one further generated surface, and wherein the four individual coils of the two coil arrangements are distributed in the circumferential direction on the further generated surface.

3. A coil system according to claim 1 wherein a radial separation exists between the individual coils situated on the first generated surface and the individual coils situated on the further generated surface.

4. A coil system according to claim 1 wherein the coils situated on the at least one first generated surface or the field gradient coils situated on the at least one further generated surface are saddle-shaped coils.

5. A coil system according to claim 4, wherein the saddle-shaped coils on the first non-quadratic, tube-shaped surface are rotated by at least approximately 45° in the circumferential direction relative to the saddle-shaped coils on the further non-quadratic, tube-shaped surface.

6. A coil system according to claim 4 wherein adjacent ones of the saddle-shaped coils as viewed in the circumferential direction respectively have frontal arc sections situated next to one another or overlapping one another.

7. A coil system according to claim 4 wherein some of said individual coils are toroidal coils and wherein a length of the coil arrangement that encompasses the saddle-shaped coils is smaller in the z-direction than a length in the z-direction of the coil arrangement that encompasses the toroidal coils.

8. A coil system according to claim 1 wherein the frontal coils are flat toroids.

9. A coil I system according to claim 8, wherein the toroids lie on the further generated surface of the field gradient coils.

10. A coil system according to claim 1 wherein coil pairs or coil arrangements are respectively formed from individual coils with identical shape.

11. A coil system according to claim 1 wherein coil pairs or coil arrangements are respectively formed from individual coils of which at least individuals exhibit different coil cross-sections.

12. A coil system according to claim 1 comprising coil pairs arranged orthogonal to one another, said coil pairs being composed of individual coils for generation of the magnetic field components.

13. A coil system according to claim 1 comprising individual coils with different winding cross-sections or of conductors with different cross-sections.

14. A coil system according to claim 1 comprising a cooling arrangement that cools at least some of the individual coils.

15. A coil system according to claim 1 comprising parts made from magnetically soft material on an exterior of the working space for field amplification or field shielding.

16. A coil system according to claim 1 comprising a position detector that detects a position of the magnetic body within the working space.

17. A coil system according to claim 1 comprising a computer that controls operation of the its individual coils.

* * * * *